United States Patent [19]

McFarlane

[11] 4,129,128
[45] Dec. 12, 1978

[54] SECURING DEVICE FOR CATHETER PLACEMENT ASSEMBLY

[76] Inventor: Richard H. McFarlane, 506 Tyler Rd., St. Charles, Ill. 60174

[21] Appl. No.: 771,187

[22] Filed: Feb. 23, 1977

[51] Int. Cl.² ............................................... A61M 5/00
[52] U.S. Cl. ................................ 128/133; 128/214 R; 128/DIG. 26
[58] Field of Search ................ 128/214 R, 214.4, 221, 128/133, DIG. 26

[56] References Cited

U.S. PATENT DOCUMENTS

| 2,727,512 | 12/1955 | Muller | 128/133 |
| 2,882,898 | 4/1959 | Holmes | 128/133 |
| 3,782,383 | 1/1974 | Thompson et al. | 128/214 R |

*Primary Examiner*—Dalton L. Truluck

[57] ABSTRACT

A securing device for a catheter placement assembly comprising a pair of oppositely-extending wings connected together by an upstanding portion with an axial through hole along a line of symmetry between the wings and said through hole being adapted to be positioned over a catheter in position so that tape may be applied to the wings to hold the catheter placement assembly in position.

5 Claims, 4 Drawing Figures

SECURING DEVICE FOR CATHETER PLACEMENT ASSEMBLY

FIELD OF THE INVENTION

This invention relates to a device for securing a catheter placement assembly in position on the arm of a wearer.

BACKGROUND OF THE INVENTION

In the past, there have been numerous types of catheter placement devices wherein a needle which is sheathed in a relatively flexible sleeve is inserted into the vein and, thereafter, the needle is removed. In other instances, a needle is inserted directly into the vein. In any event, it is often necessary, particularly where intravenous feeding is involved, to secure the assembly to the arm of a wearer for extended periods of time. In the past, the unit has been taped in a relatively difficult operation to the arm. This invention is of an improved device which is adapted to be positioned over the catheter placement assembly, once it has been inserted, and which facilitates securing the assembly to the arm.

It is, accordingly, an object of this invention to provide an inexpensive unit which is well adapted for securing a catheter placement assembly, such as the type used in intravenous feeding, to the arm of a wearer, and which can be easily removed and which can be dressed easily and which protects the puncture point from infection.

In accordance with this general object, the instant invention will now be described with reference to the accompanying drawings wherein a unit of the device to size has been illustrated.

DESCRIPTION OF PREFERRED EMBODIMENT

Figure 1:
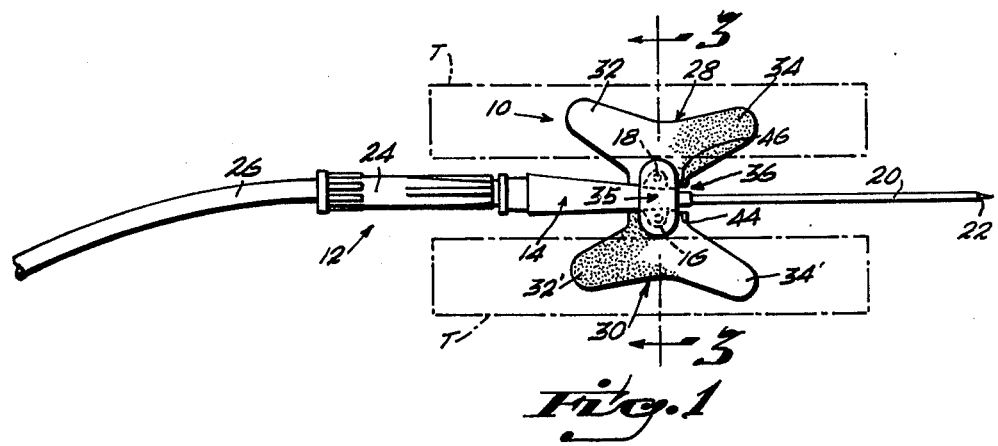
FIG. 1 is a plan view of the securing device illustrating its use.
Figure 2:
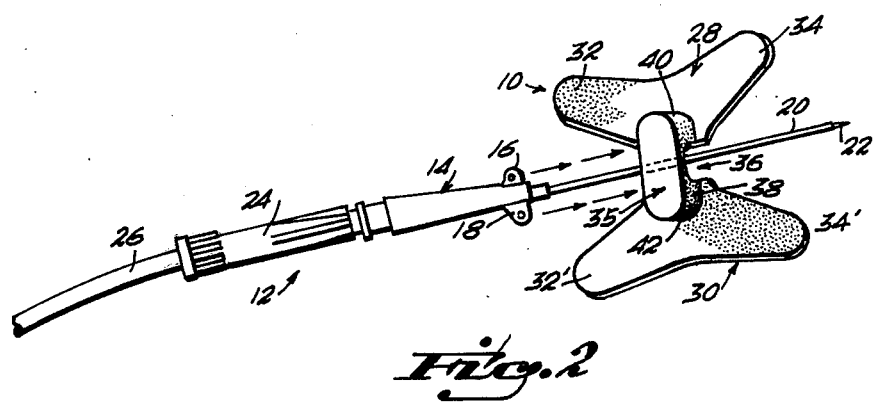
FIG. 2 is a perspective view of the securing device.
Figure 4:
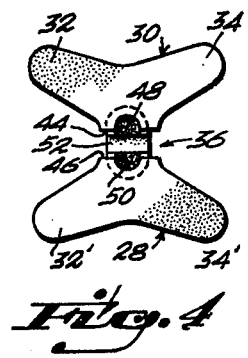
FIG. 4 is a bottom plan view of the device.

It will be helpful to the reader in understanding the use of the instant invention to refer to the co-pending application, Ser. No. 614,707 of a Catheter Placement Assembly. Although not exclusively for use with such a specific catheter placement assembly, the instant invention will be understood on reference to that application. Referring now to the drawings, it is seen in FIGS. 1 and 2 that the securing device is generally designated by the numeral 10, and that it is intended to be positioned over the ears 16 and 18 of a catheter body for introduction of intravenous fluids as is generally indicated by the numeral 12, preferably, after the needle 22 has been withdrawn axially from the flexible catheter 20. A suitable fitting 24 is provided, and this fitting is connected to a tube 26 which in turn is used for introducing intravenous feeding. The securing device 10 comprises a pair of wings 28 and 30, each composed in the preferred embodiment of diverging portions 32 and 34 and 32' and 34'. The wings are joined by a body 35 with side walls 38, 40 and 42 extending upwardly of the upper surface of the wings and in the side walls of which there is an axial cut-out, as at 36 defined in the walls 44 and 46, with the space between the walls at the cut-out being sized for passage of the catheter body and snug receipt thereof. As is seen in FIG. 4, the underside of the ears 48 and 50 are received within a cavity in the body with the dome 52 comprising a groove in the roof to nestle about the body.

In use, once the needle and catheter have been inserted into the vein, it is adapted to be firmly secured in position on the arm by applying the securing device of the instant invention over the ears 16 and 18 and, thereafter, the unit may be taped down conveniently by the tape T indicated by the dotted lines in FIG. 1. In the preferred embodiment, the unit is made of molded polyethylene, and the unit is somewhat bendable along the centerline of the unit 52 which accommodates application of the unit in a general snap-like manner preferably. It is, therefore, easy to apply and is well adapted for holding the catheter placement assembly in position.

With respect to the catheter placement assembly in Ser. No. 614,707, which has relatively small ears on the body, this device can be taped directly to the skin of a wearer; however, it is generally difficult to do and requires a skilled technician using a sling type bandage. Many placement assemblies do not have ears at all. Various types of methods are used to tape them into position; however, because the unit must be manipulated for the main purpose, namely, to insert them into a vein, protruding devices are generally avoided. This invention, it is seen is of a device which can be readily positioned over a catheter placement assembly, after it is in place, which by means of the dome or roof, captivates it in position with the outwardly-extending wings resting on the arm of a patient whereupon they may be taped readily in the position desired with the tape being away from the axial centerline of the device and, hence, the puncture site. The device, once in position, cannot readily rotate or move axially, which is a safety feature, since the devices are often installed over long periods of time as an intravenous feeding. Notwithstanding this, the securing device may be readily removed simply by holding it in position in the central zone while the tape is removed from the wing zones. Moreover, the catheter placement assembly is positioned and held firmly without direct contact of the catheter placement assembly itself so that the same can be manipulated, as when changing the material introduced into the patient. Finally, the puncture site is not covered by tape. An ointment can be used and a bandaid directly at the puncture site without interference from the tape securing the catheter placement assembly. All of the foregoing are advantages and objects of the instant invention.

Figure 3:
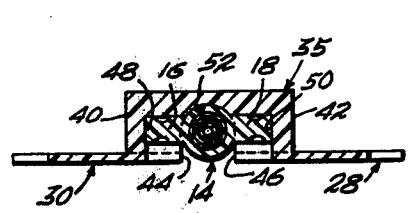
FIG. 3 is a view in cross section taken along the plane indicated by the line 3—3 of FIG. 1 and looking in the direction of the arrows.

In the preferred embodiment, the axial distance between the tips of the diverging portions of the wings 32 and 34 are about one and one-quarter inches, while the thickness of them is about 0.20 inch, and the distance between portions of the wings 32 and 32' is about one and one-quarter inches. The height of the dome or body is of a height to accommodate nestling over the particular catheter placement assembly which is utilized and a cavity is provided in it, as indicated, which is sized to nestle yieldably over the catheter placement assembly with the plane of engagement of the wing and the lower portion of the catheter placement assembly being at about a common level as indicated in FIG. 3. In other words, the cavity conforms to the shape of the particular catheter placement assembly to which the securing device is installed and for installation it may be hingedly opened about the line of symmetry to be restored by the plastic memory to its normal position as shown in FIGS. 1, 3 and 4, defining what may be described as a yieldable clamp type action about the hinge joint composed of the roof or bridge joining the wings in which the cavity is located.

What is claimed is:

1. A securing device for a catheter placement assembly wherein said assembly defines a flow through passageway and includes:

a flexible catheter having a pointed distal end which in use extends through a skin puncture site into the vein of a patient after a rigid needle has been withdrawn from the assembly and wherein the catheter includes a proximal end exteriorly of the site adjacent the puncture;

a catheter body having a proximal supply end including a fitting adapted to be connected to a supply tube and a distal end zone connected to the proximal catheter end at a zone of juncture;

a pair of oppositely facing ears extending from the body adjacent the zone of juncture, each of said ears and said zone of juncture being of a common predetermined size and shape;

said securing device comprising a molded body of relatively thin, plastic material of inverted cup-shaped form having a top surface and a depending skirt with a terminal edge spaced from the top surface, said body defining a socket bounded by a proximal and distal portion, each with a cut-out and spaced side portions connecting the proximal and distal portion, and said socket being sized and configured to nestle in mating relation over and above the ears with the distal end zone of the body extending axially through the cut-outs, said securing device comprising wings extending laterally from the terminal edge of each of said side skirt portion and each of said wings including:

a proximal and distally-extending diverging portion having a smooth upper surface, said wing being adapted to overlay the skin of a patient to provide an anchoring surface outboard of the axial centerline of the assembly and puncture site to secure the assembly in position on the skin of a patient by strips of tape extending parallel to the assembly and over the smooth upper surface extending axially and distally therefrom.

2. The device as set forth in claim 1 wherein said securing device is of one piece molded polyethylene.

3. The device as set forth in claim 6 wherein the axial distance between the distal and proximal ends of the diverging portions of the wings are about one and one-quarter inches.

4. The device as set forth in claim 3 wherein the thickness of said wings is about 0.020 inch.

5. The device as set forth in claim 1 wherein said top surface comprises a hinge means and said cut-outs are adapted to be opened and closed to receive and release the ears from the socket, said top surface comprising a hinge means having an axially-extending axis for flexing movement of the side portions of said skirt.

* * * * *